United States Patent [19]

Sato et al.

[11] Patent Number: 5,451,687
[45] Date of Patent: Sep. 19, 1995

[54] PROCESS FOR PRODUCING O,O'-DIACYLTARTARIC ANHYDRIDE AND PROCESS FOR PRODUCING O,O'-DIACYLTARTARIC ACID

[75] Inventors: Haruyo Sato, Nagoya; Sakie Nakai, Tokoname; Toshihiro Fujino, Kuwana, all of Japan

[73] Assignee: Toray Industries, Inc., Japan

[21] Appl. No.: 158,424

[22] Filed: Nov. 29, 1993

[30] Foreign Application Priority Data

Nov. 30, 1992 [JP] Japan ................... 4-321019

[51] Int. Cl.⁶ ............. C07D 307/34; C07C 69/76; C07C 59/255
[52] U.S. Cl. ................... 549/253; 560/81; 560/96; 560/98; 560/99; 562/585
[58] Field of Search .......... 549/253; 562/585; 560/81, 96, 98, 99

[56] References Cited

U.S. PATENT DOCUMENTS

| | | | |
|---|---|---|---|
| 4,318,819 | 3/1982 | Malloy et al. | 252/184 |
| 4,318,820 | 3/1982 | Malloy et al. | 252/184 |
| 4,562,264 | 12/1985 | Gude et al. | 549/261 |
| 4,664,834 | 5/1987 | Forsberg | 549/233 |

FOREIGN PATENT DOCUMENTS

| | | |
|---|---|---|
| 22147 | 4/1982 | Hungary . |
| 22711 | 6/1982 | Hungary . |
| 34720 | 4/1985 | Hungary . |
| 55339 | 5/1991 | Hungary . |
| 55770 | 6/1991 | Hungary . |
| 948556 | 2/1964 | United Kingdom . |

OTHER PUBLICATIONS

March, Advanced Org. Chem. 3rd Edition (1985).
Butler et al, JACS 55, p. 2605 (1933).
Chem. Abst. 115(23):255981f (1991).
Chem. Abst. 117(5):48319x (1991).
Chem. Abst. 104(13):109235x (1985).
Chem. Abst. 98(9): 71698t (1982).
Chem. Abst 97:21590h (1982).
Fenton, JCS, 69, pp. 546-562 (1896).
"Note on the Preparation of Dibenzoyl-d-tartaric Acid," C. L. Butler and L. H. Cretcher, *Notes*, pp. 2605-2607, Jun. 1933.

*Primary Examiner*—Cecilia Tsang
*Attorney, Agent, or Firm*—Austin R. Miller

[57] ABSTRACT

An industrial process for producing O,O'-diacyltartaric anhydride with high purity and high efficiency is disclosed. According to the process of the invention, a carboxylic acid of the formula (I):

$$R^1COOH \qquad (I)$$

(wherein $R^1$ represents $C_1$-$C_4$ alkyl group; phenyl group; or phenyl group substituted with 1-5 $C_1$-$C_4$ alkyl groups or with 1-5 halogen atoms) is reacted with tartaric acid in the presence of a chlorinating agent.

30 Claims, No Drawings

PROCESS FOR PRODUCING O,O'-DIACYLTARTARIC ANHYDRIDE AND PROCESS FOR PRODUCING O,O'-DIACYLTARTARIC ACID

BACKGROUND OF THE INVENTION

I. Field of the Invention

This invention relates to a process for producing O,O'-diacyltartaric anhydride, and to a process for producing O,O'-diacyltartaric acid therefrom.

II. Description of the Related Art

Optically active O,O'-diacyltartaric anhydrides are useful compounds and have various uses. For example, optically active monoamides which are useful as packings of chromatography are obtained by reacting the optically active O,O'-diacyltartaric anhydrides with amines (U.S. Pat. Nos. 4,318,819 and 4,318,820). By reacting an optically active O,O'-diacyltartaric anhydride with a racemic amine, racemic amino acid, racemic hydroxy acid, racemic aminoalcohol and a racemic alcohol, respectively, diastereomers are formed, and these diastereomers can be optically resolved by chromatography or by fractional crystallization. For example, it has been reported that β-blocker which is an aminoalcohol can be optically resolved by chromatography (J. Chromatogr. 316, P605-616 (1984)), and that thymolol which is also a β-blocker is optically resolved by fractional crystallization (Dutch Patent No. 8500939).

O,O'-diacetyltartaric anhydride and O,O'-dibenzoyltartaric anhydride are known as O,O'-diacyltartaric anhydrides. As the process for producing these O,O'-diacyltartaric anhydrides, (1) a process wherein 1 mole of L-tartaric acid is reacted with 4.9 moles of acetic anhydride in the presence of a concentrated sulfuric acid to produce O,O'-diacetyl-L-tartaric anhydride (Organic Syntheses Coll. Vol. IV p.242 (1963)); (2) a process wherein 1 mole of L-tartaric acid is reacted with 3.2 moles of benzoyl chloride to produce O,O'-dibenzoyl-L-tartaric anhydride (J. Am. Chem. Soc. 55, p.2605 (1933)); and (3) a process wherein 1 mole of tartaric acid is reacted with 2 moles of benzoyl chloride in a solvent and then thionyl chloride is added, the reaction being carried out in the presence of ferric chloride, zinc chloride or aluminum chloride as a catalyst (Hungarian patent No. 34720).

In the processes (1) and (2) described above, not less than 3 moles of an acid anhydride or acid chloride is used per one mole of tartaric acid. Thus, it is necessary to remove the carboxylic acid produced as a by-product, so that it is difficult to obtain optically active O,O'-diacyltartaric anhydride with a high purity. In the process (3), expensive acid halide is necessary. Further, if ferric chloride is used as a catalyst, although the yield is high, the reaction product is undesirably colored. On the other hand, if zinc chloride or aluminum chloride is used as the catalyst, the yield is lower than in the case of using ferric chloride.

On the other hand, optically active O,O'-diacyltartaric acids produced from O,O'-diacyltartaric anhydrides are useful for racemic resolution of amines. Conventionally, O,O'-dibenzoyltartaric acid which is a representative of O,O'-diacyltartaric acids is produced by the following methods: (i) a method in which O,O'-dibenzoyltartaric anhydride is heated in water to hydrolyze the anhydride and the resultant is cooled to obtain crystals of O,O'-dibenzoyltartaric acid (J. Am. Chem. Soc., 55, 2605 (1933)); and (ii) a method in which O,O'-dibenzoyltartaric anhydride is hydrolyzed in a mixed dichloromethane and small amount of water under a pressure of 1.5–5 atm, and then the resultant is cooled to obtain crystals of O,O'-dibenzoyltartaric acid (Hungarian patent 22147).

In the above-described method (i), upon hydrolysis of O,O'-dibenzoyltartaric anhydride, the produced O,O'-dibenzoyltartaric acid is separated as an oil. When this oil is crystallized, agglomerates of crystals are formed, and the crystals are adhered to the walls and to the stirrer of the apparatus so that they cannot be removed from the reaction apparatus. Thus, the operability is low, so that this process is not suited for industrial production. On the other hand, in the above-described method (ii), although the operability is good, harmful dichloromethane is used in a large amount and the yield per one batch is low.

SUMMARY OF THE INVENTION

Accordingly, an object of the present invention is to provide a process for producing O,O'-diacyltartaric anhydride with high yield and high purity, which does not necessitate the use of an acid halide so that production can be carried out inexpensively.

Another object of the present invention is to provide a process for producing O,O'-diacyltartaric anhydride from an acid halide by which O,O'-diacyltartaric anhydride with high yield and high purity is obtained and by which the product is not undesirably colored.

Still another object of the present invention is to provide a process for producing O,O'-diacyltartaric acid with high yield and high operability without forming agglomerates of the product.

That is, the present invention provides a process for producing O,O'-diacyltartaric anhydride comprising reacting a carboxylic acid of the formula (I):

$$R^1COOH \qquad (I)$$

(wherein $R^1$ represents $C_1$–$C_4$ alkyl group; phenyl group; or phenyl group substituted with 1 or 2 $C_1$–$C_4$ alkyl groups or with 1 or 2 halogen atoms) with tartaric acid in the presence of a chlorinating agent.

The present invention also provides a process for producing O,O'-diacyltartaric anhydride comprising reacting a carboxylic chloride of the formula (II):

$$R^1COCl \qquad (II)$$

(wherein $R^1$ represents $C_1$–$C_4$ alkyl group; phenyl group; or phenyl group substituted with 1 or 2 $C_1$–$C_4$ alkyl groups or with 1 or 2 halogen atoms) with tartaric acid in the presence of a chlorinating agent and in the absence of a catalyst.

The present invention still further provides a process for producing O,O'-diacyltartaric anhydride comprising reacting a carboxylic anhydride of the formula (III):

$$(R^1CO)_2O \qquad (III)$$

(wherein $R^1$ represents $C_1$–$C_4$ alkyl group; phenyl group; or phenyl group substituted with 1 or 2 $C_1$–$C_4$ alkyl groups or with 1 or 2 halogen atoms) with tartaric acid in the presence of a chlorinating agent.

The present invention still further provides a process for producing O,O'-diacyltartaric anhydride of the formula (IV):

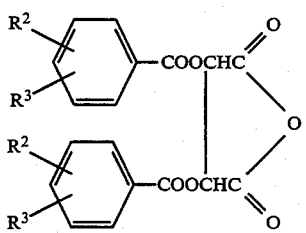

(wherein R² and R³, which may be the same or different, represent hydrogen atom, halogen atom or C₁–C₄ alkyl group) comprising reacting an aromatic carboxylic chloride of the formula (VI):

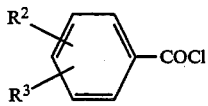

(wherein R² and R³ which may be the same or different, represent hydrogen atom, halogen atom or C₁–C₄ alkyl group) with tartaric acid in the presence of boron trifluoride as a catalyst.

The present invention still further provides a process for producing O,O′-diacyltartaric anhydride of the formula (IV):

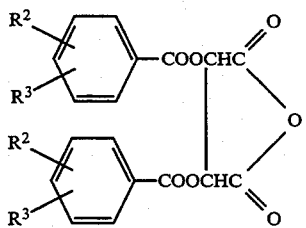

(wherein R² and R³ which may be the same or different, represent hydrogen atom, halogen atom or C₁–C₄ alkyl group) comprising reacting an aromatic carboxylic anhydride of the formula (VII):

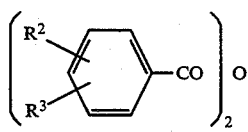

(wherein R² and R³ which may be the same or different, represent hydrogen atom, halogen atom or C₁–C₄ alkyl group) with tartaric acid in the presence of boron trifluoride as a catalyst.

The present invention still further provides a process for producing O,O′-diacyltartaric acid of the formula (VIII):

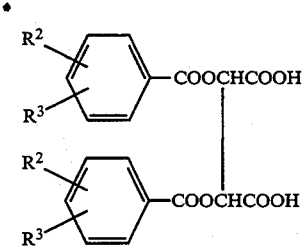

(wherein R² and R³, which may be the same or different, represent hydrogen atom, halogen atom or C₁–C₄ alkyl group) comprising hydrolyzing an aromatic carboxylic anhydride of the formula (IV):

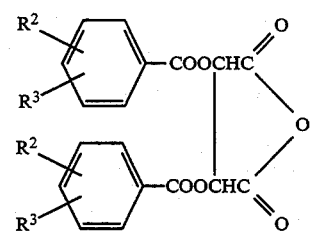

(wherein R² and R³ which may be the same or different represent hydrogen atom, halogen atom or C₁–C₄ alkyl group) said process being carried out in the presence of an organic solvent which is immiscible with water.

By the process of the present invention, O,O′-diacyltartaric anhydride can be inexpensively and industrially produced with high yield and high purity. Further, by the process of the present invention, O,O′-diacyltartaric acid can be produced with high yield and high operability without forming agglomerates of the product.

DETAILED DESCRIPTION OF THE PREFERRED EMBODIMENTS

As mentioned above, according to a first aspect of the present invention, a process for producing O,O′-diacyltartaric anhydride is provided, which comprises reacting a carboxylic acid of the formula (I):

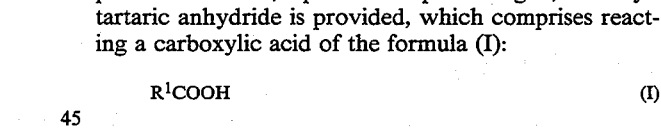

(wherein R¹ represents C₁–C₄ alkyl group; phenyl group; or phenyl group substituted with 1 or 2 C₁–C₄ alkyl groups or with 1 or 2 halogen atoms) with tartaric acid in the presence of a chlorinating agent. Examples of the carboxylic acid represented by the formula (I) (hereinafter referred to as "carboxylic acid (I)" for short) include lower aliphatic carboxylic acids such as acetic acid, propionic acid and butyric acid; benzoic acid; mono-substituted aromatic carboxylic acids such as o-toluic acid, m-toluic acid, p-toluic acid, o-chlorobenzoic acid, m-chlorobenzoic acid and p-chlorobenzoic acid; and di-substituted aromatic carboxylic acids such as 3,4-dimethylbenzoic acid.

The process for producing O,O′-diacyltartaric anhydride from carboxylic acid (I) and tartaric acid may be considered as comprising three reactions, that is, the reaction in which carboxylic acid (I) is converted to an acid chloride by the chlorinating agent; the reaction in which the hydroxyl groups in tartaric acid are O-acylated by the acid chloride; and the reaction in which the tartaric acid derivative or tartaric acid reacts with carboxylic chlorides to hetero-acid anhydrides, and followed to tartaric anhydrides and its derivatives (this is hereinafter referred to as "dehydrate"). The chlorinating reaction of carboxylic acid (I) and the O-acylation reaction of tartaric acid may proceed at the same temperature or at different temperatures. In general, in cases where carboxylic acid (I) is a lower aliphatic carboxylic acid, these reactions can proceed in the same temperature, and in cases where carboxylic acid (I) is an aromatic carboxylic acid, the O-acylation reaction usually proceeds at a higher temperature than the chlorination reaction of the aromatic carboxylic acid. Therefore, in cases where carboxylic acid (I) is a lower aliphatic carboxylic acid, the chlorination reaction, O-acylation reaction and the dehydration reaction can simultaneously proceed by adding the chlorinating agent, while in cases where carboxylic acid (I) is an aromatic carboxylic acid, it is preferred to first convert the aromatic carboxylic acid to the acid chloride by the chlorinating agent, and then to carry out the O-acylation reaction and the dehydration reaction.

In cases where a carboxylic chloride is used as an O-acylating reagent of tartaric acid as in the conventional processes, 2 moles of carboxylic chloride is consumed for the O-acylation of the two hydroxyl groups in tartaric acid per 1 mole of tartaric acid, and simultaneously, 1 mole of carboxylic chloride is consumed for the dehydration of the two carboxyl groups of the tartaric acid derivative or tartaric acid, and 1 mole of carboxylic acid is produced as a by-product. Similarly, in cases where an acid anhydride is used as the O-acylating reagent, 2 moles of acid anhydride is consumed for the O-acylation of the two hydroxyl groups in tartaric acid per 1 mole of tartaric acid, and simultaneously, 1 mole of acid anhydride is consumed for the dehydration of the two carboxyl groups in the tartaric acid derivative or tartaric acid, and 4 moles of carboxylic acid is produced as a by-product. Since the difference in the reaction rates of the O-acylation reaction and the dehydration reaction is small, it is difficult to separately carry out these reactions. Therefore, in the conventional processes, at least 3 moles of carboxylic chloride or carboxylic anhydride is necessary per 1 mole of tartaric acid.

In any of the conventional processes, as the O-acylating reagent, an acid chloride or an acid anhydride is used, and no other O-acylating reagent of tartaric acid is known. That is, to use a carboxylic acid as the starting material for producing O,O'-diacyltartaric anhydride is not known. This is because that it is believed by those skilled in the art that when chlorinating the carboxylic acid, the secondary hydroxyl groups in tartaric acid are also chlorinated by the chlorinating agent.

Surprisingly, the present inventors discovered that the chlorinating reaction of the carboxylic acid can proceed preferentially to the chlorination of the hydroxyl groups of tartaric acid so that the carboxylic acid can be converted to an acid chloride in the reaction system without accompanying chlorination of the hydroxyl groups of tartaric acid. Further, the carboxylic acid produced as a by-product can be converted again to any acid chloride by the chlorinating agent. Thus, carboxylic acids which are less expensive than acid chlorides and acid anhydrides can be employed as the starting material. Further, the amount of the carboxylic acid can be reduced to 2 moles in comparison with 3 moles of acid chloride or acid anhydride in the conventional processes, and removal of the carboxylic acid produced as a by-product is not necessary, so that O,O'-diacyltartaric anhydride can be produced with high purity and high yield.

The chlorinating reaction of the carboxylic acid preferentially proceeds to the chlorinating reaction of secondary hydroxyl groups in tartaric acid presumably because the solubility of tartaric acid in organic solvents is lower than that of the carboxylic acid, so that the chlorination of the carboxylic acid which exists in a larger amount in the organic solvent occurs preferentially to the chlorination of the hydroxyl groups and carboxylic groups of tartaric acid.

The, stoichiometric amount of carboxylic acid (I) is 2 moles per 1 mole of tartaric acid. Thus, the amount of carboxylic acid (I) per 1 mole of tartaric acid is usually 2.0–2.8 moles, preferably 2.0–2.4 moles. Use of more than 2.8 moles of carboxylic acid (I) is not preferred because the removal of the carboxylic acid produced as a by-product or excess acid chloride is more troublesome accordingly.

Since 1 mole of chlorinating agent is necessary for chlorinating 1 mole of carboxylic acid, at least 3 moles of the chlorinating agent is necessary per 1 mole of tartaric acid. Thus, the amount of the chlorinating agent used is usually 3.0–6.0 moles, preferably 3.0–4.5 moles per 1 mole of tartaric acid. If the amount of the chlorinating agent is less than 3.0 moles per 1 mole of tartaric acid, carboxylic acid (I) is not quantitatively converted to the acid chloride and the yield of the O,O'-diacyltartaric anhydride is decreased. If the amount is more than 6.0 moles, the cost of the reactant is high, so that it is not preferred.

As the chlorinating agent for chlorinating carboxylic acid (I), known chlorinating agents such as phosphorus pentachloride, phosphorus trichloride, thionyl chloride and the like may be employed. Among these, those which do not interfere with the O-acylation reaction and which do not contaminate in the produced O,O'-diacyltartaric anhydride crystals after the O-acylation reaction are preferred. Thus, thionyl chloride which can be exhausted from the reaction system after being converted to hydrogen chloride gas and $SO_2$ gas is preferred.

As the solvent used for the process, any solvent which does not modify the produced O,O'-diacyltartaric anhydride and which does not interfere the O-acylation reaction may be employed. Examples of the solvents include aromatic solvents such as benzene, toluene, xylene and chlorobenzene; ethers such as dioxane; and aliphatic hydrocarbons such as hexane and cyclohexane.

The chlorination reaction is usually carried out at room temperature to 110° C., although the preferred temperature varies depending on the carboxylic acid and the chlorinating agent employed. In cases where the carboxylic acid is an aliphatic acid, the O-acylation reaction of tartaric acid is usually carried out at 30°–160° C., preferably 40°–140° C. In cases where the carboxylic acid is an aromatic acid, O-acylation reaction of tartaric acid is usually carried out at 100°–200° C., preferably 110°–170° C. The reaction time may be appropriately selected depending on the reaction temperature and other reaction conditions, and is usually 1–40 hours.

The method for reacting tartaric acid and carboxylic acid (I) will now be described. Tartaric acid, carboxylic acid (I) and a solvent, if any, are supplied to a reaction vessel and the mixture is heated. To this solution or slurry, a chlorinating agent is added. Alternatively, tartaric acid, carboxylic acid (I), the chlorinating agent and the solvent, if any, may be simultaneously supplied. These methods are suitable when carboxylic acid (I) is a lower aliphatic carboxylic acid so that the O-acylation reaction proceeds at a relatively low temperature. In cases where carboxylic acid (I) is an aromatic carboxylic acid so that the O-acylation reaction proceeds at a higher temperature than the chlorination reaction of carboxylic acid (I), carboxylic acid (I) is first converted to an acid chloride by the chlorinating agent such as thionyl chloride, then tartaric acid is added, and then the temperature is raised to carry out the O-acylation reaction. In this case, tartaric acid may be supplied to the reaction vessel from the beginning of the process together with carboxylic acid (I). When converting the carboxylic acid produced as a by-product to the acid chloride, the temperature is lowered and the chlorinating agent is added.

After the reactions, the desired O,O'-diacyltartaric anhydride can easily be separated by known methods such as filtration, washing, filtration after condensation and the like. The separated O,O'-diacyltartaric anhydride has a high purity, and keeps the optical activity of the tartaric acid if the tartaric acid used has an optical activity. If a solid carboxylic acid (I) which is an O-acylating agent is unfortunately contaminated, the carboxylic acid may be removed by recrystallizing the product from an organic solvent such as toluene, acetonitrile or acetone, or by treating the product with a chlorinating agent such as thionyl chloride so as to convert the carboxylic acid to a liquid acid chloride.

In a preferred mode according to the first aspect of the present invention, an aromatic carboxylic acid is employed as carboxylic acid (I) and a catalyst is used. By adding a catalyst, the reaction can be carried out under mild conditions. That is, according to this mode, there is provided a process for producing O,O'-diacyltartaric anhydride of the formula (IV):

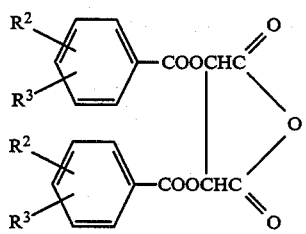
(IV)

(wherein $R^2$ and $R^3$ which may be the same or different, represent hydrogen atom, halogen atom or $C_1$–$C_4$ alkyl group) comprising reacting an aromatic carboxylic acid of the formula (V):

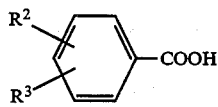
(V)

(wherein $R^2$ and $R^3$ represent the same meanings as in formula (IV)) with tartaric acid in the presence of a chlorinating agent and a catalyst.

In this process, the aromatic carboxylic acid represented by the formula (V) (hereinafter referred to as "aromatic carboxylic acid (V)" for short) is used in an amount of usually 1.8 to 4 moles, preferably 2.0 to 2.4 moles per 1 mole of tartaric acid. If the amount of aromatic carboxylic acid (V) is smaller than the lower limit of the range mentioned above, the product is contaminated with unreacted tartaric acid, so that it is not preferred. Use of the aromatic carboxylic acid (V) in an amount larger than the upper limit of the range mentioned above is also not preferred because it is costly.

In this process, the chlorinating agent co-exists in the reaction system. Examples of the chlorinating agent are the same as mentioned above, and thionyl chloride is preferred in this process too. The amount of the chlorinating agent is usually 1.4 to 3 moles, preferably 1.5 to 2.0 moles per 1 mole of aromatic carboxylic acid (v).

In this process, a catalyst co-exists in the reaction system. Examples of the catalyst include Lewis acids such as ferric chloride, aluminum chloride, zinc chloride, boron trifluoride and the like. The amount of the catalyst used is usually 0.001 to 0.2 moles, preferably 0.002 to 0.10 mole per 1 mole of tartaric acid. The total amount of the catalyst may be supplied to the reaction vessel before the beginning of the process. Alternatively, a part of the catalyst may be supplied to the reaction vessel before the beginning of the process, and additional catalyst may be added during the reaction.

Although not required, it is preferred to carry out the process in the presence of an organic solvent because the produced O,O'-diacyltartaric anhydride is not solidified in the reaction vessel, so that the process can be carried out with good operability. Examples of the organic solvent include aliphatic hydrocarbons such as heptane, octane and nonane; and aromatic hydrocarbons such as benzene, toluene and xylene. Among these, benzene, toluene and xylene are preferred. Two or more organic solvents may be employed in combination. The solvent is used in an amount of usually 0.5 to 10 times by weight, preferably 1 to 5 times by weight the amount of the tartaric acid used. If the amount of the solvent is smaller than the lower limit of the range mentioned above, the concentration of the produced O,O'-diacyltartaric anhydride in the slurry is high and so the stirring of the slurry is difficult, so that it is not preferred. On the other hand, if the amount of the solvent is larger than the upper limit of the range mentioned above, a reaction apparatus with large volume is necessary, and the productivity is decreased, so that it is not preferred. The organic solvent may be added either before the beginning of the reaction or during the reaction, the former being preferred.

Aromatic carboxylic acid (V) and tartaric acid can be reacted by, for example, as follows: A mixture of tartaric acid, aromatic carboxylic acid (V) and an organic solvent, if any, is heated to an appropriate temperature (described below), then a chlorinating agent such as thionyl chloride is slowly added, then a catalyst is added, and then the resulting mixture is further heated (aged) to carry out the reaction. Alternatively, a mixture of tartaric acid, aromatic carboxylic acid (V), a catalyst, and an organic solvent, if any, is heated to an appropriate temperature, then a chlorinating agent such as thionyl chloride is slowly added, and the resulting mixture is further aged. Still alternatively, a mixture of tartaric acid, aromatic carboxylic acid (V), a catalyst, a chlorinating such as thionyl chloride, and an organic solvent, if any, is slowly heated to an appropriate temperature and the mixture is further aged to carry out the reaction. Thus, the catalyst may be added before beginning of the reaction or during the reaction. Alternatively, the catalyst may be added before beginning of the reaction and during the reaction.

This process is usually carried out at 40°–170° C., preferably at 60°–150° C. If the reaction temperature is low, the reaction time is long, and if the reaction temperature is high, the reaction time is short. That is, if the reaction temperature is near the lower limit of the above-mentioned range, the reaction time may be 20–50 hours, and if the reaction temperature is near the upper limit of the above-mentioned range, the reaction time may be 1–3 hours. If the temperature is high, a decomposition reaction may occur. If the reaction temperature is in the middle of the above-mentioned range, the reaction time may be in between the above-mentioned reaction time.

The desired O,O'-diacyltartaric anhydride may be collected by collecting the crystals directly from the reaction product by filtration, or by adding a solvent to the reaction product, cooling the resultant to precipitate crystals, and collecting the crystals by filtration. The separated O,O'-diacyltartaric anhydride has a high purity, and keeps the optical activity of the tartaric acid if the tartaric acid used has an optical activity.

In a second aspect of the present invention, a process for producing O,O'-diacyltartaric anhydride is provided, in which acid chloride or acid anhydride is employed as the starting material. That is, the present invention provides a process for producing O,O'-diacyltartaric anhydride comprising reacting a carboxylic chloride of the formula (II):

$$R^1COCl \qquad (II)$$

(wherein $R^1$ represents $C_1$–$C_4$ alkyl group; phenyl group; or phenyl group substituted with 1 or 2 $C_1$–$C_4$ alkyl groups or with 1 or 2 halogen atoms) with tartaric acid in the presence of a chlorinating agent and in the absence of a catalyst. The present invention also provides a process for producing O,O'-diacyltartaric anhydride comprising reacting a carboxylic anhydride of the formula (III):

$$(R^1CO)_2O \qquad (III)$$

(wherein $R^1$ represents $C_1$–$C_4$ alkyl group; phenyl group; or phenyl group substituted with 1 or 2 $C_1$–$C_4$ alkyl groups or with 1 or 2 halogen atoms) with tartaric acid in the presence of a chlorinating agent.

Examples of the carboxylic chloride represented by the formula (II) (hereinafter also referred to as "carboxylic chloride (II)" for short) include lower aliphatic carboxylic chlorides such as acetyl chloride, propionyl chloride and butyloyl chloride; benzoyl chloride; mono-substituted aromatic carboxylic chlorides such as o-toluoyl chloride, m-toluoyl chloride, p-toluoyl chloride, o-chlorobenzoyl chloride, m-chlorobenzoyl chloride and p-chlorobenzoyl chloride; and di-substituted aromatic carboxylic chlorides such as 3,4-dimethylbenzoyl chloride. Examples of the carboxylic anhydride represented by the formula (III) (hereinafter referred to as "carboxylic anhydride (III)" for short) include those corresponding to the carboxylic chlorides just mentioned above.

Similar to the process for producing O,O'-diacyltartaric anhydride described above, which utilizes carboxylic acid as a starting material, the carboxylic acid produced as a by-product of the O-acylation of tartaric acid can be converted to an acid chloride by a chlorinating agent without causing chlorination of the secondary hydroxyl groups of tartaric acid.

Therefore, the stoichiometric amount of carboxylic chloride (II) or carboxylic anhydride (III) is 2 moles per one mole of tartaric acid. Thus, carboxylic chloride (II) or carboxylic anhydride (III) is used in an amount of usually 2.0–2.8 moles, preferably 2.0–2.4 moles per 1 mole of tartaric acid. If it is used more than 2.8 moles per 1 mole of tartaric acid, the removal of the carboxylic acid produced as a by-product and excess carboxylic chloride (II) or carboxylic anhydride (III) is more difficult accordingly.

Since 1 mole of a chlorinating agent is necessary for chlorinating 1 mole of the carboxylic acid produced as a by-product, at least 1 mole of chlorinating agent is necessary per 1 mole of tartaric acid when carboxylic chloride (II) is used as the O-acylating agent. Thus, the chlorinating agent is used usually in an amount of 1.0–2.0 moles, preferably 1.0–1.5 moles per 1 mole of tartaric acid. If the amount of the chlorinating agent is less than 1.0 mole, the carboxylic acid produced as a by-product is not quantitatively converted to the acid chloride, so that the yield of the O,O'-diacyltartaric anhydride is decreased. On the other hand, if the amount of the chlorinating agent is more than 2.0 moles, the cost of the reactant is high, so that it is not preferred. In cases where the O-acylating agent is carboxylic anhydride (III), if 2 moles of carboxylic anhydride (III) is used per 1 mole of tartaric acid, if the amount of the chlorinating agent is 1 mole, 1 mole of carboxylic acid produced as a by-product remains unreacted. However, if the carboxylic acid produced as a by-product is liquid, the unreacted carboxylic acid does not influence the purity of the produced O,O'-diacyltartaric anhydride at all. In cases where the carboxylic acid produced as a by-product is solid, the by-product may contaminate the produced O,O'-diacyltartaric anhydride. Thus, in this case, the amount of the chlorinating agent is usually 1.0–4.0 moles, preferably 1.0–3.0 moles per 1 mole of tartaric acid. Thus, by using the chlorinating agent in an equimolar amount to the carboxylic acid produced as a by-product, solid carboxylic acid can be eliminated as a liquid acid chloride from the desired product and the produced acid chloride can be effectively used as an O-acylating agent, so that the yield of O,O'-diacyltartaric anhydride can be further promoted.

As the chlorinating agent, those described above for the process utilizing carboxylic acid (I) can be used, and thionyl chloride is preferred.

As the solvent, those described above for the process utilizing carboxylic acid (I) can be used.

The chlorination of the carboxylic acid produced as a by-product is usually carried out at a temperature from room temperature to 110° C. In cases where the carboxylic acid is an aliphatic carboxylic acid, the O-acylation reaction of tartaric acid is usually carried out at 30°–160° C., preferably 40°–140° C., and in cases where the carboxylic acid is an aromatic carboxylic acid, the O-acylation reaction of tartaric acid is usually carried out at 100°–200° C., preferably 110°–170° C., although the preferred temperature varies depending on the carboxylic acid produced as a by-product and on the chlorinating agent. The reaction time may be appropriately selected depending on the reaction temperature and other reaction conditions, and is usually 1–40 hours.

The reaction between tartaric acid and carboxylic chloride (II) or carboxylic anhydride (III) may be carried out, for example, as follows: Tartaric acid, carboxylic chloride (II) or carboxylic anhydride (III) and an organic solvent, if any, are supplied to a reaction vessel and O-acylation and dehydration reactions are carried out. Then a chlorinating agent is added to carry out chlorination of the carboxylic acid produced as a by-product and simultaneously O-acylation reaction and dehydration reaction. Alternatively, tartaric acid, carboxylic chloride (II) or carboxylic anhydride (III), the chlorinating agent, and the organic solvent, if any, may be simultaneously supplied to the reaction vessel. These methods are suitable for cases where lower aliphatic carboxylic chloride or lower aliphatic carboxylic anhydride is used so that the O-acylation reaction proceeds at a relatively low temperature. In cases where an aromatic carboxylic chloride or an aromatic carboxylic anhydride is employed so that O-acylation of tartaric acid proceeds at a higher temperature than the chlorination of the carboxylic acid produced as a by-product, tartaric acid is first O-acylated and dehydrated by the carboxylic chloride or the carboxylic anhydride, then the carboxylic acid produced as a by-product is converted to an acid chloride by a chlorinating agent after lowering the temperature of the reaction system, and then the temperature of the reaction system is again raised to carry out O-acylation and dehydration reactions.

The above-described process can be carried out without using a catalyst. As demonstrated by the examples described below, even without a catalyst, satisfactory high purity and high yield may be attained and the product is not undesirably colored.

After the reactions, the desired O,O'-diacyltartaric anhydride can easily be separated by known methods such as filtration, washing, filteration after condensation and the like. The separated O,O'-diacyltartaric anhydride has a high purity, and keeps the optical activity of the tartaric acid if the tartaric acid used has an optical activity. If a solid carboxylic acid produced as a by-product is unfortunately contaminated, the carboxylic acid may be removed by recrystallizing the product from an organic solvent such as toluene, acetonitrile or acetone, or by treating the product with a chlorinating agent such as thionyl chloride so as to convert the carboxylic acid to a liquid acid chloride.

According to a third aspect of the present invention, a process for producing O,O'-diacyltartaric anhydride from an aromatic carboxylic chloride or an aromatic carboxylic anhydride with high purity and high yield is provided. That is, the present invention provides a process for producing O,O'-diacyltartaric anhydride of the formula (IV):

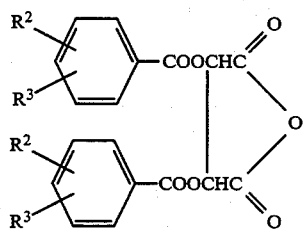 (IV)

(wherein $R^2$ and $R^3$ which may be the same or different represent hydrogen atom, halogen atom or $C_1$–$C_4$ alkyl group) comprising reacting an aromatic carboxylic chloride of the formula (VI):

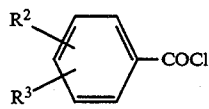 (VI)

(wherein $R^2$ and $R^3$ which may be the same or different represent hydrogen atom, halogen atom or $C_1$–$C_4$ alkyl group) or an aromatic carboxylic anhydride of the formula (VII):

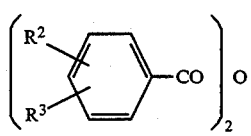 (VII)

(wherein $R^2$ and $R^3$ which may be the same or different, represent hydrogen atom, halogen atom or $C_1$–$C_4$ alkyl group) with tartaric acid in the presence of boron trifluoride as a catalyst.

The specific catalyst employed in this process is boron trifluoride. In the conventional processes for reacting tartaric acid with aromatic carboxylic chloride or aromatic carboxylic anhydride, a catalyst such as ferric chloride, zinc chloride or aluminum chloride may be employed. However, if ferric chloride is employed, the product is undesirably colored, and if zinc chloride or aluminum chloride is employed, the yield is low. In contrast, if boron trifluoride is employed, the yield is higher than in cases where conventional catalysts are used, and the product is not undesirably colored, so that it is very advantageous in industrial production.

Boron trifluoride is a known and commercially available compound and can also be obtained by conventional methods. For example, boron trifluoride which may be used in the process according to the present invention can be obtained by heating a mixture of sodium borofluoride, boron trioxide and concentrated sulfuric acid. Alternatively, commercially available boron trifluoride is absorbed by ether or the like and the resultant may be used in the process. In cases where the boron trifluoride produced by heating the mixture of sodium borofluoride, boron trioxide and concentrated sulfuric acid is used, the generated boron trifluoride may be absorbed in the reaction mixture containing tartaric acid and the solvent, and the aromatic carboxylic chloride represented by the formula (VI) (hereinafter also referred to as "aromatic carboxylic chloride (VI)" for short) or the aromatic carboxylic anhydride represented the formula (VII) (hereinafter also referred to as "aromatic carboxylic anhydride (VII) for short), if any, before the beginning of the reaction; or may be absorbed in the reaction mixture during the process. In cases where a commercially obtained boron trifluoride absorbed in ether or the like is used, the ether or the like containing boron trifluoride may be added to the reaction mixture before the beginning of the process or during the process.

The catalyst is used usually in an amount of 0.001–0.2 moles, preferably 0.002–0.10 moles per 1 mole of tartaric acid. Total amount of the catalyst may be added before the beginning of the reaction, or a part of the catalyst may be added before the beginning of the reaction and the remainder may be added during the reaction.

Although not required, it is preferred to carry out the process in the presence of an organic solvent because the produced O,O'-diacyltartaric anhydride is not solidified in the reaction vessel, so that the process can be carried out with good operability. Examples of the organic solvent include aliphatic hydrocarbons such as heptane, octane and nonane; and aromatic hydrocarbons such as benzene, toluene and xylene. Among these, benzene, toluene and xylene are preferred. Two or more organic solvents may be employed in combination. The solvent is used in an amount of usually 0.5 to 10 times by weight, preferably 1 to 5 times by weight the amount of the tartaric acid used. If the amount of the solvent is smaller than the lower limit of the range mentioned above, the concentration of the produced O,O'-diacyltartaric anhydride in the slurry is high and so the stirring of the slurry is difficult, so that it is not preferred. On the other hand, if the amount of the solvent is larger than the upper limit of the range mentioned above, a reaction apparatus with large volume is necessary, and the productivity is decreased, so that it is not preferred.

Aromatic carboxylic chloride (VI) is used usually in an amount of 2.6–5 moles, preferably 3.0–3.5 moles per 1 mole of tartaric acid. In cases where thionyl chloride co-exists in the reaction system (described below), aromatic carboxylic chloride (VI) is used usually in an amount of 1.8 to 4 moles, preferably 2.0 to 2.4 moles per 1 mole of tartaric acid. As mentioned above, in the process, aromatic carboxylic anhydride (VII) may be employed in place of aromatic carboxylic chloride (VI). In this case, aromatic carboxylic anhydride (VII) is used usually in an amount of 2.6 to 5 moles, preferably 3.0 to 3.5 moles per 1 mole of tartaric acid. In cases where thionyl chloride co-exists in the reaction system (described below), aromatic carboxylic anhydride (VII) is used usually in an amount of 0.9 to 2 moles, preferably 1.0 to 1.2 moles per 1 mole of tartaric acid. If the amount of aromatic carboxylic chloride (VI) or aromatic carboxylic anhydride (VII) is smaller than the lower limit of the range mentioned above, a part of tartaric acid remains unreacted so that the yield is decreased. On the other hand, if the amount of aromatic carboxylic chloride (VI) or aromatic carboxylic anhydride (VII) is larger than the upper limit of the range mentioned above, the cost of the reactant is high, so that it is not preferred.

In either case where tartaric acid is reacted with aromatic carboxylic chloride (VI) or aromatic carboxylic anhydride (VII), if thionyl chloride which is inexpensive co-exists, the expensive aromatic carboxylic chloride (VI) or aromatic carboxylic anhydride (VII) can be saved, and a product with high purity can be obtained, so that it is preferred. In cases where tartaric acid is reacted with aromatic carboxylic chloride (VI), the amount of thionyl chloride used is usually 0.3 to 1.5 moles, preferably 0.5 to 1.0 moles per 1 mole of aromatic carboxylic chloride (VI). In cases where tartaric acid is reacted with aromatic carboxylic anhydride (VII), the amount of thionyl chloride used is usually 0.9 to 2.5 moles, preferably 1.0 to 2.0 moles per 1 mole of aromatic carboxylic anhydride (VII). If the amount of thionyl chloride added is smaller than the lower limit of the range mentioned above, aromatic carboxylic acid may be contaminated in the product, so that it is not preferred. On the other hand, if the amount of thionyl chloride is larger than the upper limit of the range mentioned above, the cost of the reactant is high, so that it is not preferred.

Aromatic carboxylic chloride (VI) and tartaric acid may be reacted, for example, as follows: That is, a mixture of tartaric acid, the catalyst and a solvent is heated to an appropriate temperature (described below), then aromatic carboxylic chloride (VI) is added to the mixture, and then the resulting mixture is allowed to further react. Alternatively, a mixture of tartaric acid, the catalyst, aromatic carboxylic chloride (VI) and a solvent, if any, is slowly heated to a prescribed temperature. In cases where thionyl chloride co-exists, the process can be carried out, for example, as follows: That is, a mixture of tartaric acid, the catalyst, and a solvent is heated to an appropriate temperature, aromatic carboxylic chloride (VI) is then added, the resulting mixture is allowed to react for a prescribed time, and then thionyl chloride is added. Alternatively, tartaric acid, the catalyst, aromatic carboxylic chloride (VI), thionyl chloride and a solvent, if any, is slowly heated to a prescribed temperature. Still alternatively, a mixture of tartaric acid, the catalyst and a solvent is heated to an appropriate temperature and a mixture of aromatic carboxylic chloride (VI) and thionyl chloride is added to the reaction mixture.

Aromatic carboxylic anhydride (VII) and tartaric acid may be reacted, for example, as follows: That is, a mixture of tartaric acid, the catalyst and a solvent is heated to an appropriate temperature (described below), then aromatic carboxylic anhydride (VII) is added to the mixture, and then the resulting mixture is allowed to further react. Alternatively, a mixture of tartaric acid, the catalyst, aromatic carboxylic anhydride (VII) and a solvent, if any, is slowly heated to a prescribed temperature. In cases where thionyl chloride co-exists, the process can be carried out, for example, as follows: That is, a mixture of tartaric acid, the catalyst, and a solvent is heated to an appropriate temperature, aromatic carboxylic anhydride (VII) is then added, the resulting mixture is allowed to react for a prescribed time, and then thionyl chloride is added. Alternatively, tartaric acid, the catalyst, aromatic carboxylic anhydride (VII), thionyl chloride and a solvent, if any, is slowly heated to a prescribed temperature. Still alternatively, a mixture of tartaric acid, the catalyst and a solvent is heated to an appropriate temperature and a mixture of aromatic carboxylic anhydride (VII) and thionyl chloride is added to the reaction mixture.

This process is usually carried out at 40°–170° C., preferably at 60°–150° C. If the reaction temperature is low, the reaction time is long, and if the reaction temperature is high, the reaction time is short. If the temperature is high, a decomposition reaction may occur. That is, if the reaction temperature is near the lower limit of the above-mentioned range, the reaction time may be 20–50 hours, and if the reaction temperature is near the upper limit of the above-mentioned range, the reaction time may be 1–3 hours. If the reaction temperature is in the middle of the above-mentioned range, the reaction time may be in between the above-mentioned reaction time.

The desired O,O'-diacyltartaric anhydride may be collected by collecting the crystals directly from the reaction product by filtration, or by adding a solvent to the reaction product, cooling the resultant to precipitate crystals, and collecting the crystals by filtration. The separated O,O'-diacyltartaric anhydride has a high purity, and keeps the optical activity of the tartaric acid if the tartaric acid used has an optical activity.

According to a fourth aspect of the present invention, a process for producing O,O'-diacyltartaric acid of the formula (VIII):

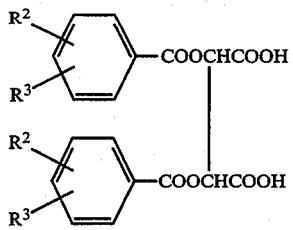

(VIII)

$R^2$ and $R^3$ which may be the same or different represent hydrogen atom, halogen atom or $C_1$–$C_4$ alkyl group) is provided, which comprises hydrolyzing an aromatic carboxylic anhydride of the formula (IV):

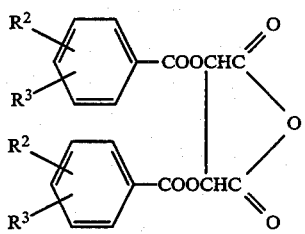

(IV)

(wherein $R^2$ and $R^3$, which may be the same or different, represent hydrogen atom, halogen atom or $C_1$–$C_4$ alkyl group) said process being carried out in the presence of an organic solvent which is immiscible with water.

The O,O'-diacyltartaric anhydride which is a starting material of this process can be obtained by conventional methods as well as by the above-described methods according to the present invention.

In this process, the term "an organic solvent which is immiscible with water" means an organic solvent whose solubility in water is not more than 2 wt % at any temperature between 20°–90° C. Examples of the organic solvent immiscible with water which may be employed in the process include aromatic hydrocarbons such as benzene, toluene and xylene; aliphatic hydrocarbons such as hexane and octane; and chlorinated hydrocarbons such as 1,2-dichloroethane, 1,1,2-trichloroethane and chlorobenzene. Among these, benzene, toluene, xylene and chlorobenzene are preferred. Two or more solvents may be employed in combination.

The amount of the organic solvent used is usually 0.01 to 0.5 times by weight, preferably 0.03 to 0.2 times by weight the amount of the O,O'-diacyltartaric anhydride. If the amount of the organic solvent is smaller than the lower limit of this range, formation of agglomerates is not sufficiently prevented, so that it is not preferred. Use of the organic solvent in an amount larger than the upper limit of the above-mentioned range is also not preferred from the view point of economy and ease of operation.

The amount of water to be added for the hydrolysis is not less than equimolar to the amount of the O,O'-diacyltartaric anhydride to be hydrolyzed. To attain good operability when the hydrolyzed O,O'-diacyltartaric acid in the form of oil is crystallized, water is added usually in an amount of 0.5 to 10 times by weight, preferably 1.5 to 5 times by weight the amount of O,O'-diacyltartaric anhydride. If the amount of water is smaller than the lower limit of this range, the concentration of the product in the slurry after crystallizing the oil is so high that the stirring is difficult, so that it is not preferred.

Hydrolysis may be carried out by, for example, heating a mixture of O,O'-diacyltartaric anhydride and water at a temperature of 70°–100° C. The reaction time is usually 0.5–5 hours, although it depends on the compound hydrolyzed. The pressure may be atmospheric pressure or a pressure higher than atmospheric pressure. The organic solvent which is immiscible with water may be added before the hydrolysis reaction, or after the hydrolysis reaction at which the produced O,O'-diacyltartaric acid is in the form of oil.

Crystals of O,O'-diacyltartaric acid after hydrolysis can be obtained by slowly cooling the reaction mixture after hydrolysis containing O,O'-diacyltartaric acid in the form of oil. It is preferred to add seed crystals for effectively carrying out the process. After hydrolysis, O,O'-diacyltartaric acid in the form of oil is separated from the reaction system. However, the temperature at which the oil is crystallized slightly varies depending on the amount of the organic solvent added and the type of the compound. In order to attain good operability and uniform crystal size, in case of producing O,O'-di-p-toluoyltartaric acid, for example, seed crystals of O,O'-di-p-toluoyltartaric acid may be added at a temperature of about 63° C. and the reaction mixture may then be slowly cooled. Once the crystallization started, stirring is continued keeping the temperature to completely crystallize the oil. In case of producing O,O'-di-benzoyltartaric acid, seed crystals of O,O'-dibenzoyltartaric acid may be added at a temperature of about 55° C. and the reaction mixture may then be slowly cooled. Once the crystallization started, stirring is continued keeping the temperature to completely crystallize the oil. If the added seed crystals are converted to oil before the crystallization started, by adding additional seed crystals and waiting the starting of crystallization, the same effects may be obtained.

The desired product can be collected by cooling the thus obtained reaction slurry to room temperature and by filtering the crystals.

By this process, O,O'-diacyltartaric acid can be produced with a high yield and good operability without a trouble that the produced O,O'-diacyltartaric acid hydrate adheres to the walls and to the stirrer of a reaction apparatus such that it cannot be removed from the reaction apparatus.

EXAMPLES

The invention will now be described by way of examples thereof. It should be noted, however, the examples are presented for illustration purpose only and should not be interpreted in any restrictive way.

The amount of O,O'-diacyltartaric anhydride in the filtrate of the reaction product was determined by reacting the O,O'-diacyltartaric anhydride with isopropylamine to form monoamide of the O,O'-diacyltartaric anhydride, and by analyzing the obtained monoamide by high performance liquid chromatography (HPLC). The optical purity was determined by hydrolyzing the O,O'-diacyltartaric anhydride to form O,O'-diacyltartaric acid and by analyzing the obtained O,O'-diacyltartaric acid by HPLC using CHIRACEL OJ (commercially available from DAICEL CHEMICAL INDUSTRIES, LTD., Osaka, Japan).

Example 1

To a 200 ml four-necked flask equipped with a thermometer, dropping funnel, condenser, and a stirrer, 15.0 g (0.100 mole) of L-tartaric acid, 18.0 g of toluene and 30.0 g (0.220 moles) of p-toluic acid were supplied. Keeping the temperature of the reaction mixture at 80°–90° C., 29.8 g (0.250 moles) of thionyl chloride was dropped from the dropping funnel for 1 hour under stirring. After completion of the dropping, the mixture was stirred for another 1 hour at this temperature and then the mixture was heated at 120° C. for 2 hours under stirring while refluxing toluene and while exhausting generated $SO_2$ and hydrogen chloride gas from the upper portion of the condenser by slightly reducing the pressure. During this operation, crystals were precipitated. The temperature of the oil bath in which the flask was placed was lowered to 80° C., thereby keeping the temperature of the reaction mixture at 75°–85° C. Under these conditions, 15.0 g (0.126 moles) of thionyl chloride was dropped into the mixture for 1 hour. The mixture was then aged for another 1 hour under these conditions and then the bath temperature was raised to 130° C. The mixture was allowed to react at this temperature for 6 hours under reflux. During this step, the temperature of the mixture was 115° C. To the resulting mixture, 40.1 g of toluene was added and the resultant was cooled to room temperature. The reaction mixture was subjected to filtration and the obtained crystals were washed with 23.0 g of toluene. The resultant was dried under reduced pressure at 60° C. to obtain 33.2 g (0.090 moles) of O,O'-di-p-toluoyl-L-tartaric anhydride in the form of white crystals. The yield was 90.1%. The content of p-toluic acid in the crystals was 0.3 wt %, and the melting point of the crystals was 204°–205° C. The optical purity was 99.5% ee.

IR: 2974, 2954, 1883, 1809, 1732, 1707, 1610, 1267, 1058, 1019 cm$^{-1}$

NMR: 2.42 ppm (6H), 6.64 ppm (2H), 7.35–8.02 ppm (8H)

Example 2

To a 300 ml four-necked flask equipped with a thermometer, dropping funnel, condenser, and a stirrer, 30.0 g (0.200 moles) of L-tartaric acid, 36.1 g of toluene and 53.7 g (0.440 moles) of benzoic acid were supplied. Keeping the temperature of the reaction mixture at 80°–90° C. 59.6 g (0.500 moles) of thionyl chloride was dropped from the dropping funnel for 1 hour under stirring. After completion of the dropping, the mixture was stirred for another 1 hour at this temperature and then the mixture was heated at 110° C. for 3 hours under stirring while exhausting generated $SO_2$ and hydrogen chloride gas from the upper portion of the condenser by slightly reducing the pressure. During this operation, crystals were precipitated. The temperature of the oil bath in which the flask was placed was lowered to 80° C., thereby keeping the temperature of the reaction mixture at 75°–85° C. Under these conditions, 28.6 g (0.240 moles) of thionyl chloride was dropped into the mixture for 1 hour. The mixture was then aged for another 1 hour under these conditions and then the mixture was stirred at 110° C. for 6 hours. To the resulting mixture, 68.1 g of toluene was added and the resultant was cooled to room temperature. The reaction mixture was subjected to filtration and the obtained crystals were washed with 40.0 g of toluene. The resultant was dried under reduced pressure at 50° C. to obtain 54.8 g (0.161 moles) of O,O'-dibenzoyl-L-tartaric anhydride in the form of white crystals. The yield was 80.6%. The content of benzoic acid in the crystals was 0.2 wt %, and the melting point of the crystals was 194°–196° C. The optical purity was 99.5% ee.

IR: 2968, 2950, 1880, 1823, 1738, 1706, 1568, 1266, 1058, 1027, 709 cm$^{-1}$

NMR: 6.75 ppm (2H), 7.45–8.20 ppm (10H)

Example 3

To a 50 ml two-necked flask equipped with a condenser and a dropping funnel, 3.0 g (0.020 moles) of DL-tartaric acid, 4.0 g of toluene, 6.3 g (0.046 moles) of p-toluic acid and 6.5 g of thionyl chloride (0.055 moles) were supplied and the mixture was stirred for 3 hours in an oil bath having a temperature of 90° C. Then the temperature of the bath was raised to 130° C. and the mixture was stirred for 4 hours under these conditions while exhausting generated $SO_2$ and hydrogen chloride gas from the upper portion of the condenser by slightly reducing the pressure. The bath temperature was then lowered to 90° C. and 3.6 g (0.030 moles) of thionyl chloride was added to the mixture, followed by stirring for 1 hour at this temperature. The bath temperature was raised to 130° C., and the mixture was stirred for 3 hours under these conditions. Then 30 g of toluene was added so as to dissolve any solid matter and the resulting mixture was gradually cooled to room temperature. The reaction product was then subjected to filtration, and the obtained crystals were washed and dried at 60° C. under reduced pressure to obtain 5.9 g (0.016 moles) of O,O'-di-p-toluoyl-DL-tartaric anhydride in the form of white crystals (yield: 80%).

Example 4

To a 50 ml two-necked flask equipped with a condenser and a dropping funnel, 4.3 g (0.072 moles) of acetic acid and 4.5 g (0.030 moles) of L-tartaric acid were supplied. To the mixture, 14.2 g (0.119 moles) of thionyl chloride was dropped for 4 hours under stirring in an oil bath having a temperature of 67° C. The resultant was stirred for another 2 hours under these conditions. After cooling the resultant to room temperature, 3.5 g of toluene was added and the mixture was stirred. The precipitated crystals were collected by filtration and washed and dried under reduced pressure at 50° C. to obtain 5.6 g of white crude crystals. The obtained crude crystals were recrystallized from acetic acid/toluene to obtain 4.2 g (0.019 moles) of O,O'-diacetyl-L-tartaric anhydride. The yield was 63% and the melting point of the product was 132°–134° C.

Example 5

To a 50 ml two-necked flask equipped with a condenser and a dropping funnel, 6.0 g of xylene, 10.3 g (0.066 moles) of o-chlorobenzoic acid, 4.5 g (0.030 moles) of L-tartaric acid and 9.4 g (0.079 moles) of thionyl chloride were supplied and the mixture was stirred for 3 hours in an oil bath having a temperature of 90° C. The bath temperature was raised to 130° C. and the mixture was stirred under these conditions for 4.5 hours while exhausting generated $SO_2$ and hydrogen chloride gas from the upper portion of the condenser by slightly reducing the pressure. The bath temperature was then lowered to 90° C. and 5.1 g (0.043 moles) of thionyl chloride was added to the mixture, followed by stirring for 1.5 hours under these conditions. The bath temperature was raised to 130° C., and the mixture was stirred for 2.5 hours under these conditions. Then 30 g of toluene was added and the resulting mixture was gradually cooled to room temperature under stirring. The precipitated crystals were collected by filtration, washed and dried at 50° C. under reduced pressure to obtain 6.6 g (0.016 moles) of O,O'-bis(o-chlorobenzoyl)-L-tartaric anhydride in the form of white crystals (yield: 54%). The analytical data of the product were as follows:

melting point: 165°–169° C.

IR: 2936, 1888, 1805, 1735, 1590, 1249, 1142, 1131, 1057, 1047, 952, 738 $cm^{-1}$

NMR: 6.80 ppm (2H), 7.40–8.15 ppm (8H)

Example 6

To a 50 ml two-necked flask equipped with a condenser and a dropping funnel, 6.0 g of xylene, 8.9 g (0.066 moles) of m-toluic acid, 4.5 g (0.030 moles) of L-tartaric acid and 9.4 g (0.079 moles) of thionyl chloride were supplied and the mixture was stirred for 3 hours in an oil bath having a temperature of 85° C. The bath temperature was raised to 130° C. and the mixture was stirred under these conditions for 3.5 hours while exhausting generated $SO_2$ and hydrogen chloride gas from the upper portion of the condenser by slightly reducing the pressure. The bath temperature was then lowered to 85° C. and 5.8 g (0.049 moles) of thionyl chloride was added to the mixture, followed by stirring for 1.5 hours under these conditions. The bath temperature was raised to 130° C., and the mixture was stirred for 5 hours under these conditions. Then 30 g of xylene was added and the resulting mixture was gradually cooled to room temperature under stirring. The precipitated crystals were collected by filtration, washed and dried at 50° C. under reduced pressure to obtain 8.4 g (0.023 moles) of O,O'-di-m-toluoyl-L-tartaric anhydride in the form of white crystals. The analytical data of the product were described below. The reaction yield including O,O'-di-m-toluoyl-L-tartaric anhydride contained in the reaction filtrate detected by HPLC analysis was 82% and the isolation yield was 76%.

melting point: 142°–147° C.

IR: 2962, 1881, 1820, 1734, 1704, 1590, 1333, 1276, 1196, 1060, 1016, 740 $cm^{-1}$

NMR: 2.40 ppm (6H), 6.68 ppm (2H), 7.35–8.00 ppm (8H)

Example 7

To a 300 ml reaction vessel equipped with a thermometer, dropping funnel, condenser, and a stirrer, 30.0 g (0.200 mole) of D-tartaric acid, 66.0 g (0.440 moles) of 3,4-dimethylbenzoic acid and 40 g of toluene were supplied. Keeping the temperature of the reaction mixture at 80°–90° C., 59.6 g (0.500 moles) of thionyl chloride was dropped from the dropping funnel for 1 hour under stirring. After completion of the dropping, the mixture was stirred for another 1 hour at this temperature and then the mixture was heated at 120° C. for 2 hours under stirring while exhausting generated $SO_2$ and hydrogen chloride gas from the upper portion of the condenser by slightly reducing the pressure. During this operation, crystals were precipitated. The temperature of the oil bath in which the flask was placed was lowered to 80° C., thereby keeping the temperature of the reaction mixture at 75°–85° C. Under these conditions, 28.6 g (0.240 moles) of thionyl chloride was dropped into the mixture for 1 hour. The mixture was then aged for another 1 hour under these conditions and then the bath temperature was raised to 120° C. The mixture was stirred at this temperature for 6 hours. To the resulting mixture, 68.0 g of toluene was added and the resultant was cooled to room temperature. The reaction mixture was subjected to filtration and the obtained crystals were washed with 40.0 g of toluene. The resultant was dried under reduced pressure at 40° C. to obtain 71.4 g (0.180 moles) of O,O'-bis(3,4-dimethylbenzoyl)-D-tartaric anhydride in the form of white crystals. The melting point of the product was 180°–182° C. and the yield was 90.1%.

Example 8

To a 300 ml reaction vessel equipped with a stirrer, thermometer, condenser and a dropping funnel, 30 g of D-tartaric acid, 70 g of toluene, 0.12 g of ferric chloride and 53.7 g of benzoic acid were supplied, and the mixture was heated to 90° C. While keeping this temperature, 83.7 g of thionyl chloride was added from the dropping funnel for 6 hours and the resulting mixture was aged at 105°–110° C. for another 1 hour to carry out the reaction. The reaction mixture was then cooled to room temperature and the precipitated crystals were collected by filtration, followed by drying to obtain 61.8 g of O,O'-dibenzoyl-D-tartaric anhydride in the form of pale yellow crystals. HPLC analysis revealed that the purity of the O,O'-dibenzoyl-D-tartaric anhydride was 100% (yield: 90.9%).

Example 9

To a 300 ml reaction vessel equipped with a stirrer, thermometer, condenser and a dropping funnel, 30 g of D-tartaric acid, 70 g of toluene, 0.12 g of ferric chloride and 59.9 g of p-toluic acid were supplied, and the mixture was heated to 90° C. While keeping this temperature, 83.7 g of thionyl chloride was added from the dropping funnel for 6 hours and the resulting mixture was aged at 105°–110° C. for another 1 hour to carry out the reaction. The reaction mixture was then cooled to room temperature and the precipitated crystals were collected by filtration, followed by drying to obtain 67.2 g of O,O'-di-p-toluoyl-D-tartaric anhydride in the form of pale yellow crystals (purity: 100%, yield: 91.3%).

Example 10

To a 300 ml reaction vessel equipped with a stirrer, thermometer, condenser and a dropping funnel, 30 g of D-tartaric acid, 70 g of toluene, 0.12 g of ferric chloride, 83.7 g of thionyl chloride and 53.7 g of benzoic acid were supplied, and the mixture was heated to 90° C. under stirring for 3 hours. While keeping this temperature, the mixture was aged for another 4 hours and the resulting mixture was heated at 105°–110° C. for another 1 hour. The reaction mixture was then cooled to room temperature and the precipitated crystals were collected by filtration, followed by drying to obtain 62.3 g of O,O'-dibenzoyl-D-tartaric anhydride in the form of pale yellow crystals (purity: 100%, yield: 91.6%).

Example 11

To a 300 ml reaction vessel equipped with a stirrer, thermometer, condenser and a dropping funnel, 30 g of D-tartaric acid, 70 g of toluene, 0.12 g of ferric chloride, 83.7 g of thionyl chloride and 59.9 g of p-toluic acid were supplied, and the mixture was heated to 90° C. under stirring for 3 hours. While keeping this temperature, the mixture was aged for another 4 hours and the resulting mixture was heated at 105°–110° C. for another 1 hour. The reaction mixture was then cooled to room temperature and the precipitated crystals were collected by filtration, followed by drying to obtain 67.7 g of O,O'-di-p-toluoyl-D-tartaric anhydride in the form of pale yellow crystals (purity: 100%, yield: 92.0%).

Example 12

To a 300 ml reaction vessel equipped with a stirrer, thermometer, condenser and a dropping funnel, 30 g of D-tartaric acid, 70 g of toluene, 0.10 g of zinc chloride and 53.7 g of benzoic acid were supplied, and the mixture was heated to 90° C. While keeping this temperature, 83.7 g of thionyl chloride was added from the dropping funnel for 6 hours and the resulting mixture was aged at 105°–110° C. for another 1 hour to carry out the reaction. The reaction mixture was then cooled to room temperature and the precipitated crystals were collected by filtration, followed by drying to obtain 58.1 g of O,O'-dibenzoyl-D-tartaric anhydride in the form of white crystals (purity: 100%, yield: 85.4%).

Example 13

To a 300 ml reaction vessel equipped with a stirrer, thermometer, condenser and a dropping funnel, 30 g of D-tartaric acid, 70 g of toluene, 1.4 g of boron trifluoride etherate in diethylether and 53.7 g of benzoic acid were supplied, and the mixture was heated to 90° C. While keeping this temperature, 83.7 g of thionyl chloride was added from the dropping funnel for 6 hours and the resulting mixture was aged at 105°–110° C. for another 1 hour to carry out the reaction. The reaction mixture was then cooled to room temperature and the precipitated crystals were collected by filtration, followed by drying to obtain 62.0 g of O,O'-dibenzoyl-D-tartaric anhydride in the form of white crystals (purity: 100%, yield: 91.2%).

Example 14

To a 300 ml reaction vessel equipped with a stirrer, thermometer, condenser and a dropping funnel, 30 g of D-tartaric acid, 70 g of toluene, 0.12 g of ferric chloride and 66.0 g of 3,4-dimethylbenzoic acid were supplied, and the mixture was heated to 90° C. While keeping this temperature, 83.7 g of thionyl chloride was added from the dropping funnel for 6 hours and the resulting mixture was aged at 105°–110° C. for another 1 hour to carry out the reaction. The reaction mixture was then cooled to room temperature and the precipitated crystals were collected by filtration, followed by drying to obtain 71.4 g of O,O'-bis(3,4-dimethylbenzoyl)-D-tartaric anhydride in the form of pale yellow crystals (purity: 100%, yield: 90.1%).

Example 15

To a 300 ml reaction vessel equipped with a stirrer, thermometer, condenser and a dropping funnel, 30 g of D-tartaric acid, 70 g of toluene, 0.12 g of ferric chloride and 68.8 g of o-chlorobenzoic acid were supplied, and the mixture was heated to 90° C. While keeping this temperature, 83.7 g of thionyl chloride was added from the dropping funnel for 6 hours and the resulting mixture was aged at 105°–110° C. for another 1 hour to carry out the reaction. The reaction mixture was then cooled to room temperature and the precipitated crystals were collected by filtration, followed by drying to obtain 74.3 g of O,O'-bis(o-chlorobenzoyl)-D-tartaric anhydride in the form of pale yellow crystals (purity: 100%, yield: 90.8%).

Example 16

To a 300 ml reaction vessel equipped with a stirrer, thermometer, condenser and a dropping funnel, 30 g of D-tartaric acid, 70 g of toluene, 0.10 g of aluminum chloride and 53.7 g of benzoic acid were supplied, and the mixture was heated to 90° C. While keeping this temperature, 83.7 g of thionyl chloride was added from the dropping funnel for 6 hours and the resulting mixture was aged at 105°–110° C. for another 1 hour to carry out the reaction. The reaction mixture was then cooled to room temperature and the precipitated crystals were collected by filtration, followed by drying to obtain 58.9 g of O,O'-dibenzoyl-D-tartaric anhydride in the form of white crystals (purity: 100%, yield: 86.6%).

Example 17

To a 300 ml four-necked flask equipped with a thermometer, dropping funnel, condenser and a stirrer, 30.0 g (0.200 moles) of L-tartaric acid and 36.1 g of toluene were supplied. From the dropping funnel, 68.0 g (0.440 moles) of p-toluic chloride was dropped for 2 hours under sufficient stirring while refluxing toluene and while exhausting generated $SO_2$ and hydrogen chloride gas from the upper portion of the condenser by slightly reducing pressure. During the dropping of p-toluic chloride, the temperature of the bath in which the flask was placed was kept 13°–15° C. higher than the temperature of the mixture. When half of p-toluic chloride was dropped, precipitation of crystals began. After dropping p-toluic chloride, the reaction mixture was aged for 1 hour under reflux. The bath temperature was then lowered to 80° C., thereby keeping the temperature of the reaction mixture at 75°–85° C. Under these conditions, 28.6 g (0.240 moles) of thionyl chloride was dropped for 1 hour. After dropping thionyl chloride, the mixture was aged for 1 hour and then the bath temperature was raised to 130° C. The mixture was stirred for 6 hours under these conditions, during which the temperature of the mixture was about 115° C. Then 68.1 g of toluene was added to the mixture and the mixture was cooled to room temperature. The reaction mixture was subjected to filtration and the obtained crystals were washed with 43.0 g of toluene. The crystals were then dried at 60° C. under reduced pressure to obtain 67.5 g (0.183 moles) of O,O'-di-p-toluoyl-L-tartaric anhydride in the form of white crystals. The yield was 91.5%. The analytical date of the obtained compound were as described below. The content of p-toluic acid in the obtained crystals was 0.1 wt % and the optical purity of the obtained product was 99.5%.

Example 18

To a 300 ml four-necked flask equipped with a thermometer, dropping funnel, condenser and a stirrer, 30.0 g (0.200 moles) of L-tartaric acid and 36.1 g of toluene were supplied. From the dropping funnel, 61.9 g (0.440 moles) of benzoyl chloride was dropped for 3 hours under sufficient stirring at 110° C. while exhausting generated $SO_2$ and hydrogen chloride gas from the upper portion of the condenser by slightly reducing pressure. When half of benzoyl chloride was dropped, precipitation of crystals began. During the dropping, the bath temperature was kept at 122°–124° C. The mixture was then aged for 2 hours at a temperature of the mixture of 110° C., and then the bath temperature was lowered to 80° C., thereby keeping the temperature of the mixture at 75°–85° C. Under these conditions, 28.6 g (0.240 moles) of thionyl chloride was dropped for 1 hour. After dropping thionyl chloride, the mixture was aged for 1 hour at this temperature and the resulting mixture was stirred at 110° C. for 6 hours. Then 68.5 g of toluene was added to the mixture and the mixture was cooled to room temperature. The reaction mixture was subjected to filtration and the obtained crystals were washed with 40.0 g of toluene. The crystals were then dried at 50° C. under reduced pressure to obtain 54.8 g (0.161 moles) of O,O'-dibenzoyl-L-tartaric anhydride in the form of white crystals (yield: 80.5%). The content of benzoic acid in the obtained crystals was 0.2 wt % and the optical purity of the obtained product was 99.5%.

Example 19

To a 50 ml two-necked flask equipped with a condenser and a dropping funnel, 3.0 g (0.020 moles) of DL-tartaric acid, 4.0 g of toluene and 8.5 g (0.055 moles) of p-toluic chloride were supplied. The mixture was stirred for 4 hours at a bath temperature of 130° C. while exhausting generated $SO_2$ and hydrogen chloride gas from the upper portion of the condenser by slightly reducing pressure. After lowering the bath temperature to 90° C., 3.0 g (0.025 moles) of thionyl chloride was added to the mixture and the mixture was stirred for 1 hour under these conditions. The bath temperature was then raised to 130° C. and the mixture was stirred for 4 hours. Then 30 g of toluene was added to the mixture to dissolve any solid matter and the resulting mixture was slowly cooled to room temperature. The generated crystals were collected by filtration, washed and dried at 60° C. under reduced pressure to obtain 5.9 g (0.016 moles) of O,O'-di-p-toluoyl-DL-tartaric anhydride in the form of white crystals.

Example 20

To a 50 ml two-necked flask equipped with a condenser and a dropping funnel, 7.3 g (0.072 moles) of acetic anhydride and 4.5 g (0.030 moles) of L-tartaric acid were supplied. The mixture was stirred for 4 hours at a bath temperature of 67° C. and then 9.5 g (0.080 moles) of thionyl chloride was dropped under stirring for 4 hours under these conditions. The resulting mixture was stirred under these conditions for another 2 hours. After cooling the reaction mixture to room temeprature, 3.5 g of toluene was added to the mixture and the resulting mixture was stirred. The generated precipitates were collected by filtration, washed and dried at 50° C. under reduced pressure to obtain 5.6 g (0.026 moles) of white O,O'-diacetyl-L-tartaric anhydride (yield: 86%). The melting point of the product was 132°–134° C.

Example 21

To a 50 ml two-necked flask equipped with a condenser and a dropping funnel, 6.0 g of xylene, 11.6 g (0.066 moles) of o-chlorobenzoic chloride and 4.5 g (0.030 moles) of L-tartaric acid were supplied. The mixture was stirred for 4.5 hours at a bath temperature of 130° C. while exhausting generated $SO_2$ and hydrogen chloride gas from the upper portion of the condenser by slightly reducing pressure. After lowering the bath temperature to 90° C., 5.1 g (0.043 moles) of thionyl chloride was added to the mixture and the mixture was stirred for 1.5 hours under these conditions. The bath temperature was then raised to 130° C. and the mixture was stirred for 2.5 hours. Then 30 g of toluene was added to the mixture and the resulting mixture was slowly cooled to room temperature under stirring. The generated crystals were collected by filtration, washed and dried at 50° C. under reduced pressure to obtain 6.6 g (0.016 moles) of O,O'-bis(o-chlorobenzoyl)-L-tartaric anhydride in the form of white crystals (yield: 54%).

Example 22

To a 50 ml two-necked flask equipped with a condenser and a dropping funnel, 6.0 g of xylene, 10.2 g (0.066 moles) of m-toluic chloride and 4.5 g (0.030 moles) of L-tartaric acid were supplied. The mixture was stirred for 3.5 hours at a bath temperature of 130° C. while exhausting generated $SO_2$ and hydrogen chloride gas from the upper portion of the condenser by slightly reducing pressure. After lowering the bath temperature to 90° C., 5.8 g <0.049 moles) of thionyl chloride was added to the mixture and the mixture was stirred for 1.5 hours under these conditions. The bath temperature was then raised to 130° C. and the mixture was stirred for 5 hours. Then 30 g of xylene was added to the mixture and the resulting mixture was slowly cooled to room temperature under stirring. The generated crystals were collected by filtration, washed and dried at 60° C. under reduced pressure to obtain 8.4 g (0.023 moles) of O,O'-di-m-toluoyl-L-tartaric anhydride in the form of white crystals. The isolation yield was 76%.

Example 23

To a 300 ml reaction vessel equipped with a thermometer, dropping funnel, condenser and a stirrer, 30.0 g (0.200 moles) of D-tartaric acid and 40 g of toluene were supplied. From the dropping funnel, 74.2 g (0.440 moles) of 3,4-dimethylbenzoyl chloride was dropped for 3 hours under sufficient stirring while refluxing toluene and while exhausting generated $SO_2$ and hydrogen chloride gas from the upper portion of the condenser by slightly reducing pressure. After dropping 3,4-dimethylbenzoyl chloride, the reaction mixture was aged for 2 hours under reflux. The bath temperature was then lowered to 80° C., thereby keeping the temperature of the reaction mixture at 75°–85° C. Under these conditions, 28.6 g (0.240 moles) of thionyl chloride was dropped for 1 hour. After dropping thionyl chloride, the mixture was aged for 1 hour at this temperature and then the mixture was stirred for 6 hours under reflux of toluene. Then 68.0 g of toluene was added to the mixture and the mixture was cooled to room temperature. The reaction mixture was subjected to filtration and the obtained crystals were washed with 40.0 g of toluene. The crystals were then dried at 40° C. under reduced pressure to obtain 71.4 g (0.180 moles) of O,O'-bis(3,4-dimethylbenzoyl)-D-tartaric anhydride. The melting point of the product was 180°–182° C. and the yield was 90.1%.

Comparative Example 1

To a 300 ml reaction vessel equipped with a stirrer, thermometer, condenser and a dropping funnel, 30 g (0.20 moles) of L-tartaric acid and 70 g of toluene were supplied. To this mixture, 89.9 g (0.64 moles) of benzoyl chloride was added from the dropping funnel for 3 hours at 90°–95° C. under stirring. The resulting mixture was aged for 1 hour at 105°–110° C. The reaction mixture was cooled to room temperature and the precipitated crystals were collected by filtration and dried to obtain 68.1 g of white crystals. HPLC analysis revealed that the purity of the obtained O,O'-dibenzoyl-L-tartaric anhydride was 76.5% (yield: 76.6%).

Comparative Example 2

To a 300 ml reaction vessel equipped with a stirrer, thermometer, condenser and a dropping funnel, 30 g of L-tartaric acid, 70 g of toluene and 0.12 g of ferric chloride were supplied. To this mixture, 62 g of benzoyl chloride was added from the dropping funnel for 3 hours at 90°–95° C. under stirring. Then 28.5 g of thionyl chloride was added from the dropping funnel for 3 hours at this temperature under stirring and the resulting mixture was aged for 1 hour at 105°–110° C. The reaction mixture was cooled to room temperature and the precipitated crystals were collected by filtration and dried to obtain 62.1 g of O,O'-dibenzoyl-L-tartaric anhydride in the form of pale yellow crystals (purity: 100%, yield: 91.3%).

Comparative Example 3

To a 300 ml reaction vessel equipped with a stirrer, thermometer, condenser and a dropping funnel, 30 g of L-tartaric acid, 70 g of toluene and 0.10 g of zinc chloride were supplied. To this mixture, 62 g of benzoyl chloride was added from the dropping funnel for 3 hours at 90°–95° C. under stirring. Then 28.5 g of thionyl chloride was added from the dropping funnel for 3 hours at this temperature under stirring and the resulting mixture was aged for 1 hour at 105°–110° C. The reaction mixture was cooled to room temperature and the precipitated crystals were collected by filtration and dried to obtain 58.1 g of O,O'-dibenzoyl-L-tartaric anhydride in the form of white crystals (purity: 100%, yield: 85.4%).

Comparative Example 4

To a 300 ml reaction vessel equipped with a stirrer, thermometer, condenser and a dropping funnel, 30 g of L-tartaric acid, 70 g of toluene and 0.12 g of ferric chloride were supplied. To this mixture, 68 g of p-toluoyl chloride was added from the dropping funnel for 3 hours at 90°–95° C. under stirring. Then 28.5 g of thionyl chloride was added from the dropping funnel for 3 hours at this temperature under stirring and the resulting mixture was aged for 1 hour at 105°–110° C. The reaction mixture was cooled to room temperature and the precipitated crystals were collected by filtration and dried to obtain 67.7 g of O,O'-di-p-toluoyl-L-tartaric anhydride in the form of pale yellow crystals (purity: 100%, yield: 92.0%).

Example 24

To a 300 ml reaction vessel equipped with a stirrer, thermometer, condenser and a dropping funnel, 30 g of L-tartaric acid, 70 g of toluene and 1.4 g of boron trifluoride etherate in diethylether were supplied. To this mixture, 89.9 g of benzoyl chloride was added from the dropping funnel for 3 hours at 90°–95° C. under stirring. The resulting mixture was aged for 1 hour at 105°–110° C. The reaction mixture was cooled to room temperature and the precipitated crystals were collected by filtration and dried to obtain 71.1 g of white crystals. HPLC analysis revealed that the purity of the obtained O,O'-dibenzoyl-L-tartaric anhydride was 86.6% (yield: 90.5%).

Example 25

To a 300 ml reaction vessel equipped with a stirrer, thermometer, condenser and a dropping funnel, 30 g of D-tartaric acid, 70 g of toluene and 1.4 g of boron trifluoride etherate in diethylether were supplied. To this mixture, 62 g of benzoyl chloride was added from the dropping funnel for 3 hours at 90°–95° C. under stirring. Then 28.5 g of thionyl chloride was added from the dropping funnel for 3 hours under the same conditions. The resulting mixture was then aged for 1 hour at 105°–110° C. The reaction mixture was cooled to room temperature and the precipitated crystals were collected by filtration and dried to obtain 61.9 g of O,O'-dibenzoyl-L-tartaric anhydride in the form of white crystals (purity: 100%, yield: 91.0%).

Example 26

To a 300 ml reaction vessel equipped with a stirrer, thermometer, condenser and a dropping funnel, 30 g of L-tartaric acid, 70 g of toluene and 1.4 g of boron trifluoride etherate in diethylether were supplied. To this mixture, 68 g of p-toluoyl chloride was added from the dropping funnel for 3 hours at 90°–95° C. under stirring. Then 28.5 g of thionyl chloride was added from the dropping funnel for 3 hours under the same conditions. The resulting mixture was aged for 1 hour at 105°–110° C. The reaction mixture was cooled to room temperature and the precipitated crystals were collected by filtration and dried to obtain 67.7 g of O,O'-di-p-toluoyl-L-tartaric anhydride in the form of white crystals (purity: 100%, yield: 92.0%).

Example 27

To a 300 ml reaction vessel equipped with a stirrer, thermometer, condenser and a dropping funnel, 30 g of L-tartaric acid, 70 g of toluene and 0.2 g of boron trifluoride etherate in diethylether were supplied. To this mixture, 68 g of p-toluoyl chloride was added from the dropping funnel for 3 hours at 90°–95° C. under stirring. Under these conditions, to this mixture, 1.2 g of boron trifluoride etherate in diethylether was added and then 28.5 g of thionyl chloride was added from the dropping funnel for 3 hours under the same conditions. The resulting mixture was aged for 1 hour at 105°–110° C. The reaction mixture was cooled to room temperature and the precipitated crystals were collected by filtration and dried to obtain 67.4 g of O,O'-di-p-toluoyl-L-tartaric anhydride in the form of white crystals (purity: 100%, yield: 91.6%).

Example 28

To a 300 ml reaction vessel equipped with a stirrer, thermometer, condenser and a dropping funnel, 30 g of L-tartaric acid, 70 g of toluene, 49.7 g of benzoic anhydride, 88.9 g of thionyl chloride and 1.4 g of boron trifluoride etherate in diethylether were supplied. The mixture was heated to 90°–95° C. for 6 hours under stirring and then the resulting mixture was aged for 1 hour at 105°–110° C. The reaction mixture was cooled to room temperature and the precipitated crystals were collected by filtration and dried to obtain 63.2 g of O,O'-dibenzoyl-L-tartaric anhydride in the form of white crystals (purity: 100%, yield: 92.9%).

Example 29

To a 300 ml reaction vessel equipped with a stirrer, thermometer, condenser and a dropping funnel, 30 g of D-tartaric acid, 70 g of toluene and 1.4 g of boron trifluoride etherate in diethylether were supplied. To this mixture, 77 g of o-chlorobenzoyl chloride was added from the dropping funnel for 3 hours at 90°-95° C. under stirring. Then 28.5 g of thionyl chloride was added from the dropping funnel for 3 hours under the same conditions. The resulting mixture was aged for 1 hour at 105°-110° C. The reaction mixture was cooled to room temperature and the precipitated crystals were collected by filtration and dried to obtain 74.3 g of O,O'-bis(o-chlorobenzoyl)-D-tartaric anhydride in the form of white crystals (purity: 100%, yield: 90.8%).

Comparative Example 5

To a 300 ml reaction vessel equipped with a stirrer, thermometer, condenser and a dropping funnel, 50 g of O,O'-di-p-toluoyl-L-tartaric anhydride and 150 g of water were supplied and the mixture was stirred at 90°-95° C. for 1 hour to carry out hydrolysis. After cooling the reaction mixture to 75° C. 0 1 g of seed crystal of O,O'-di-p-toluoyl-L-tartaric acid was added and the mixture was slowly cooled. Since oily product began to crystalize at 73° C., the mixture was stirred for 1 hour at this temperature. After completion of crystallization, the reaction slurry was cooled to room temperature and the crystals were collected by filtration. The thus obtained cake was dried to obtain 32.3 g of O,O'-di-p-toluoyl-L-tartaric acid hydrate in the form of white crystals. The content of crystal water was measured by the Karl Fischer method, which was 4.9% (yield: 58.6%). The crystals were sieved through a 20-mesh sieve and 48 wt % of the crystals passed through the sieve. The amount of the crystals which adhered to the wall or to the stirrer of the reaction apparatus so that which could not be removed from the reaction apparatus was 20.9 g which was 39.3 wt % of the total crystals produced.

Comparative Example 6

To the reaction vessel employed in Comparative Example 5, 50 g of O,O'-dibenzoyl-D-tartaric anhydride and 150 g of water were supplied and the mixture was stirred at 90°-95° C. for 1 hour to carry out hydrolysis. After cooling the reaction mixture to 55° C., 0.1 g of seed crystal of O,O'-dibenzoyl-D-tartaric acid was added and the mixture was slowly cooled. Since oily product began to crystalize at 53° C., the mixture was stirred for 1 hour at this temperature. After completion of crystallization, the reaction slurry was cooled to room temperature and the crystals were collected by filtration. The thus obtained cake was dried to obtain 28.4 g of O,O'-dibenzoyl-D-tartaric acid hydrate in the form of white crystals. The content of crystal water was measured by Karl Fischer method, which was 4.7% (yield: 1.4%). The crystals were sieved through a 20-mesh sieve and 41 wt % of the crystals passed through the sieve. The amount of the crystals which adhered to the wall or to the stirrer of the reaction apparatus so that which could not be removed from the reaction apparatus was 23.5 g which was 45.3 wt % of the total crystals produced.

Example 30

To a 300 ml reaction vessel equipped with a stirrer, thermometer and a condenser, 50 g of O,O'-di-p-toluoyl-L-tartaric anhydride and 150 g of water were supplied and the mixture was stirred at 90°-95° C. for 1 hour to carry out hydrolysis. After cooling the reaction mixture to 63° C., 5 g of toluene and 0.1 g of seed crystal of O,O'-di-p-toluoyl-L-tartaric acid were added and the mixture was slowly cooled. Since oily product began to crystalize at 61° C., the mixture was stirred for 1 hour at this temperature. After completion of crystallization, the reaction slurry was cooled to room temperature and the crystals were collected by filtration. The thus obtained cake was dried to obtain 52.7 g of O,O'-di-p-toluoyl-L-tartaric acid hydrate in the form of white crystals. The content of crystal water was measured by Karl Fischer method, which was 4.3% (yield: 96.2%). The crystals were sieved through a 20-mesh sieve and 98 wt % of the crystals passed through the sieve. The amount of the crystals which adhered to the wall or to the stirrer of the reaction apparatus so that which could not be removed from the reaction apparatus was 0.8 g which was 1.5 wt % of the total crystals produced.

Example 31

To the reaction vessel employed in Example 30, 50 g of O,O'-dibenzoyl-D-tartaric anhydride and 150 g of water were supplied and the mixture was stirred at 90°-95° C. for 1 hour to carry out hydrolysis. After cooling the reaction mixture to 50° C., 5 g of toluene and 0.1 g of seed crystal of O,O'-dibenzoyl-D-tartaric acid were added and the mixture was slowly cooled. Since oily product began to crystalize at 48° C., the mixture was stirred for 1 hour at this temperature. After completion of crystallization, the reaction slurry was cooled to room temperature and the crystals were collected by filtration. The thus obtained cake was dried to obtain 51.2 g of O,O'-dibenzoyl-D-tartaric acid hydrate in the form of white crystals. The content of crystal water was measured by Karl Fischer method, which was 4.6% (yield: 92.8%). The crystals were sieved through a 20-mesh sieve and 96 wt % of the crystals passed through the sieve. The amount of the crystals which adhered to the wall or to the stirrer of the reaction apparatus so that which could not be removed from the reaction apparatus was 1.5 g which was 2.8 wt % of the total crystals produced.

Example 32

To the reaction vessel employed in Example 30, 50 g of O,O'-di-p-toluoyl-L-tartaric anhydride, 150 g of water and 5 g of toluene were supplied and the mixture was stirred at 90°-95° C. for 1 hour to carry out hydrolysis. After cooling the reaction mixture to 63° C., 0.1 g of seed crystal of O,O'-di-p-toluoyl-L-tartaric acid was added and the mixture was slowly cooled. Since oily product began to crystalize at 61° C., the mixture was stirred for 1 hour at this temperature. After completion of crystallization, the reaction slurry was cooled to room temperature and the crystals were collected by filtration. The thus obtained cake was dried to obtain 52.8 g of O,O'-di-p-toluoyl-L-tartaric acid hydrate in the form of white crystals. The content of crystal water was measured by Karl Fischer method, which was 4.5% (yield: 96.1%). The crystals were sieved through a 20-mesh sieve and 98 wt % of the crystals passed through the sieve. The amount of the crystals which adhered to the wall or to the stirrer of the reaction apparatus so that which could not be removed from the reaction apparatus was 1.1 g which was 2.0 wt % of the total crystals produced.

Example 33

To the reaction vessel employed in Example 30, 50 g of O,O'-bis(3,4-dimethylbenzoyl)-L-tartaric anhydride and 150 g of water were supplied and the mixture was stirred at 90°–95° C. for 1 hour to carry out hydrolysis. After cooling the reaction mixture to 63° C., 5 g of toluene and 0.1 g of seed crystal of O,O'-bis(3,4-dimethylbenzoyl)-L-tartaric acid were added and the mixture was slowly cooled. Since oily product began to crystalize at 60° C., the mixture was stirred for 1 hour at this temperature. After completion of crystallization, the reaction slurry was cooled to room temperature and the crystals were collected by filtration. The thus obtained cake was dried to obtain 52.1 g of O,O'-bis(3,4-dimethylbenzoyl)-D-tartaric acid hydrate in the form of white crystals. The content of crystal water was measured by Karl Fischer method, which was 3.8% (yield: 95.9%). The crystals were sieved through a 20-mesh sieve and 96 wt % of the crystals passed through the sieve. The amount of the crystals which adhered to the wall or to the stirrer of the reaction apparatus so that which could not be removed from the reaction apparatus was 1.3 g which was 2.4 wt % of the total crystals produced.

Example 34

To the reaction vessel employed in Example 30, 50 g of O,O'-bis(o-chlorobenzoyl)-L-tartaric anhydride and 150 g of water were supplied and the mixture was stirred at 90°–95° C. for 1 hour to carry out hydrolysis. After cooling the reaction mixture to 43° C., 5 g of toluene and 0.1 g of seed crystal of O,O'-bis(o-chlorobenzoyl)-L-tartaric acid were added and the mixture was slowly cooled. Since oily product began to crystalize at 39° C., the mixture was stirred for 1 hour at this temperature. After completion of crystallization, the reaction slurry was cooled to room temperature and the crystals were collected by filtration. The thus obtained cake was dried to obtain 51.7 g of O,O'-bis(o-chlorobenzoyl)-L-tartaric acid hydrate in the form of white crystals. The content of crystal water was measured by Karl Fischer method, which was 4.8% (yield: 94.3%). The crystals were sieved through a 20-mesh sieve and 95 wt % of the crystals passed through the sieve. The amount of the crystals which adhered to the wall or to the stirrer of the reaction apparatus so that which could not be removed from the reaction apparatus was 1.9 g which was 3.5 wt % of the total crystals produced.

What we claim is:

1. A process for producing O,O'-diacyltartaric anhydride comprising reacting a carboxylic acid of the formula (I):

R¹COOH                                (I)

(wherein R¹ represents C₁–C₄ alkyl group; phenyl group; or phenyl group substituted with 1 or 2 C₁–C₄ alkyl groups or with 1 or 2 halogen atoms) with tartaric acid in the presence of a chlorinating agent.

2. The process according to claim 1, wherein R¹ is phenyl group or phenyl group substituted with 1 or 2 C₁–C₄ alkyl groups or with 1 or 2 halogen atoms.

3. The process according to claim 2, wherein the reaction is carried out at a temperature of 100°–200° C.

4. A process for producing O,O'-diacyltartaric anhydride of the formula (IV):

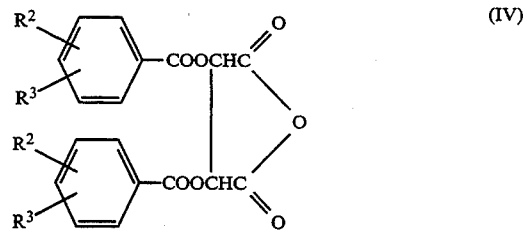

(wherein R² and R³, which may be the same or different represent hydrogen atom, halogen atom or C₁–C₄ alkyl group) comprising reacting an aromatic carboxylic acid of the formula (V):

(wherein R² and R³ represent the same meanings as in formula (IV)) with tartaric acid in the presence of a chlorinating agent and a catalyst.

5. The process according to claim 1, wherein said chlorinating agent is thionyl chloride.

6. The process according to claim 4, wherein said catalyst is a Lewis acid.

7. The process according to claim 6, wherein said Lewis acid is FeCl₃, ZnCl₂, AlCl₃ or BF₃.

8. The process according to claim 3, wherein the reaction is carried out at a temperature of 40°–200° C.

9. The process according to claim 1, wherein said carboxylic acid is used in an amount of 2.0 to 2.8 moles per 1 mole of said tartaric acid.

10. The process according to claim 1, wherein said chlorinating agent is used in an amount of 3.0 to 6.0 moles per 1 mole of said tartaric acid.

11. The process according to claim 1, wherein said tartaric acid is L- or D-tartaric acid and the produced O,O'-diacyltartaric anhydride is O,O'-diacyl-L-tartaric anhydride or O,O'-diacyl-D-tartaric anhydride having the same chirality as said L- or D-tartaric acid used as a starting material.

12. A process for producing O,O'-diacyltartaric anhydride comprising reacting a carboxylic chloride of the formula (II):

R¹COCl                                (II)

(wherein R¹ represents C₁–C₄ alkyl group; phenyl group, or phenyl group substituted with 1 or 2 C₁–C₄ alkyl groups or with 1 or 2 halogen atoms) with tartaric acid in the presence of a chlorinating agent selected from the group consisting of phosphorus pentachloride, phosphorus trichloride and thionyl chloride and in the absence of a catalyst, and Wherein the carboxylic chloride is used in an amount of 2.0 to 2.8 moles per 1 mole of said tartaric acid.

13. The process according to claim 12, wherein R¹ is phenyl group or phenyl group substituted with 1 or 2 C₁–C₄ alkyl groups or with 1 or 2 halogen atoms.

14. A process for producing O,O'-diacyltartaric anhydride of the formula (IV):

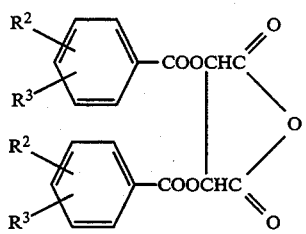

(wherein R² and R³, which may be the same or different, represent hydrogen atom, halogen atom or C₁–C₄ alkyl group) comprising reacting an aromatic carboxylic chloride of the formula (VI):

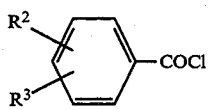

(wherein R² and R³, which may be the same or different, represent hydrogen atom, halogen atom of C₁–C₄ alkyl group) with tartaric acid in the presence of boron triflouride as a catalyst.

15. The process according to claim 12, wherein said chlorinating agent is thionyl chloride.

16. The process according to claim 12, wherein the reaction is carried out at a temperature of 40°–200° C.

17. The process according to claim 12, wherein said chlorinating agent is used in an amount of 1.0 to 2.0 moles per 1 mole of said tartaric acid.

18. The process according to claim 12, wherein said tartaric acid is L- or D-tartaric acid and the produced O,O'-diacyltartaric anhydride is O,O'-diacyl-L-tartaric anhydride or O,O'-diacyl-D-tartaric anhydride having the same chirality as said L- or D-tartaric acid used as a starting material.

19. A process for producing O,O'-diacyltartaric anhydride comprising reacting a carboxylic anhydride of the formula (III):

$(R^1CO)_2O$      (III)

(wherein R¹ represents C₁–C₄ alkyl group; phenyl group; or phenyl group substituted with 1 or 2 C₁–C₄ alkyl groups or with 1 or 2 halogen atoms) with tartaric acid in the presence of a chlorinating agent.

20. The process according to claim 19, wherein R¹ is phenyl group or phenyl group substituted with 1 or 2 C₁–C₄ alkyl groups or with 1 or 2 halogen atoms.

21. A process for producing O,O'-diacyltartaric anhydride of the formula (IV):

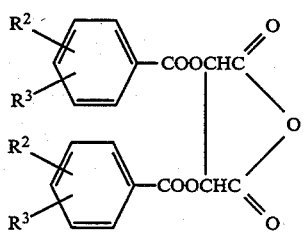

(wherein R² and R³, which may be the same or different, represent hydrogen atom, halogen atom or C₁–C₄ alkyl group) comprising reacting an aromatic carboxylic chloride of the formula (VII):

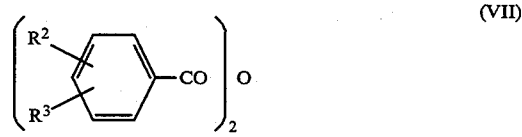

(wherein R² and R³, which may be the same or different, represent hydrogen atom, halogen atom or C₁–C₄ alkyl group) with tartaric acid in the presence of boron trifluoride as a catalyst.

22. The process according to claim 19, wherein the reaction is carried out in the presence of thionyl chloride.

23. The process according to claim 19, wherein the reaction is carried out at a temperature of 40°–200° C.

24. The process according to claim 19, wherein said carboxylic chloride is used in an amount of 0.9 to 2.0 moles per 1 mole of said tartaric acid.

25. The process according to claim 19, wherein said chlorinating agent is used in an amount of 0.9 to 2.5 moles per 1 mole of said tartaric acid.

26. The process according to claim 19, wherein said tartaric acid is L- or D-tartaric acid and the produced O,O'-diacyltartaric anhydride is O,O'-diacyl-L-tartaric anhydride or O,O'-diacyl-D-tartaric anhydride having the same chirality as said L- or D-tartaric acid used as a starting material.

27. A process for producing O,O'-diacyltartaric acid of the formula (VIII):

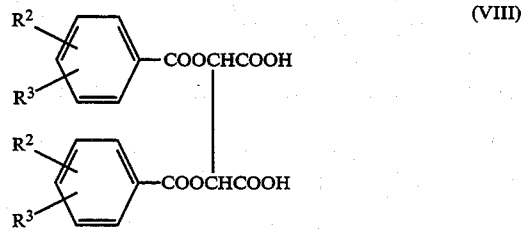

(wherein R² and R³, which may be the same or different, represent hydrogen atom, halogen atom or C₁–C₄ alkyl group) comprising hydrolyzing an aromatic carboxylic anhydride of the formula (IV):

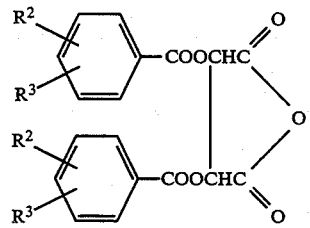

(wherein R² and R³, which may be the same or different, represent hydrogen atom, halogen atom or C₁–C₄ alkyl group) said process being carried out in the presence of an organic solvent which is immiscible with water.

28. The process according to claim 27, wherein the amount of said organic solvent is 0.01 to 0.5 times by weight the amount of said aromatic carboxylic anhydride of the formula (IV).

29. The process according to claim 27, wherein said organic solvent is benzene, toluene, xylene or chlorobenzene.

30. The process according to claim 27, wherein the hydrolysis is carried out at a temperature of 70° to 100° C.

* * * * *

UNITED STATES PATENT AND TRADEMARK OFFICE
CERTIFICATE OF CORRECTION

PATENT NO. : 5,451,687
DATED : September 19, 1995
INVENTOR(S) : Haruyo Sato et al It is certified that error appears in the above-indentified patent and that said Letters Patent is hereby corrected as shown below:

In Column 5, Line 61, delete "any" and substitute --the--.
In Column 5, Line 59, delete "the" and substitute --any--.

In Column 6, Line 12, after "The" delete the comma.

In Column 16, Line 57, delete "purpose" and substitute --purposes--.

In Column 27, Line 55, delete "1.4%" and substitute --51.4%--.

In Column 30, Line 61, delete "Wherein" and substitute --wherein--.

In Column 31, Line 23, delete "of" and substitute --or--.

Signed and Sealed this

Fifth Day of March, 1996

Attest:

BRUCE LEHMAN

Attesting Officer

Commissioner of Patents and Trademarks